United States Patent [19]

Fields, Jr.

[11] Patent Number: 5,023,369

[45] Date of Patent: Jun. 11, 1991

[54] PROCESS FOR PRODUCING N-PHOSPHONOMETHYLGLYCINE

[75] Inventor: Donald L. Fields, Jr., Manchester, Mo.

[73] Assignee: Monsanto Company, St. Louis, Mo.

[21] Appl. No.: 543,016

[22] Filed: Jun. 25, 1990

[51] Int. Cl.$^5$ ............................................. C07F 9/38
[52] U.S. Cl. ................................................. 562/17
[58] Field of Search ..................................... 562/17

[56] References Cited

U.S. PATENT DOCUMENTS

| | | | |
|---|---|---|---|
| 3,950,402 | 4/1976 | Franz | 260/502.5 |
| 3,954,848 | 5/1976 | Franz | 260/502.5 |
| 4,486,356 | 12/1984 | Bakel | 562/17 |
| 4,507,250 | 3/1985 | Bakel | 562/17 |
| 4,853,159 | 8/1989 | Riley et al. | 562/17 |

FOREIGN PATENT DOCUMENTS 0187347 7/1981 Hungary .

OTHER PUBLICATIONS

"Peroxygen Compounds in Organic Synthesis" A Technical Bulletin by INTEROX.

*Primary Examiner*—J. E. Evans
*Attorney, Agent, or Firm*—Frank D. Shearin

[57] ABSTRACT

A process is provided to produce N-phosphonomethylglycine by the oxidation of N-phosphonomethyliminodiacetic acid to form an intermediate N-phosphonomethyliminodiacetic acid-N-oxide with a peroxide in the presence of an effective amount of a catalyst selected from the group consisting of water-soluble tungsten compounds and a mixture of water-soluble tungsten compounds and a water-soluble molybdenum compound to form the intermediate, and thereafter converting the intermediate N-phosphonomethyliminodiacetic acid-N-oxide to N-phosphonomethylglycine.

13 Claims, No Drawings

PROCESS FOR PRODUCING N-PHOSPHONOMETHYLGLYCINE

BACKGROUND OF THE INVENTION

This invention relates to a process for the preparation of N-phosphonomethylglycine, and more particularly to the preparation of N-phosphonomethyliminodiacetic acid-N-oxide from N-phosphonomethyliminodiacetic acid using peroxides, which is converted to N-phosphonomethylglycine.

N-Phosphonomethylglycine, known also by its common name glyphosate, is a highly effective, commercially important, phytotoxicant useful in controlling a large variety of weeds. It is applied to the foliage of a very broad spectrum of annual and perenial grasses and broadleaf plants. Industrial uses include control of weeds along roadsides, waterways, transmission lines, in storage areas, and in other nonagricultural areas. Usually, N-phosphonomethylglycine is formulated into herbicidal compositions in the form of its various salts in solution, preferably water.

U.S. Pat. No. 3,950,402 to Franz discloses a process for the production of N-phosphonomethylglycine by forming an admixture of N-phosphonomethyliminodiacetic acid, water, and a metallic catalyst selected from the noble metals, heating the admixture to an elevated temperature (greater than 70° C. to avoid low yields) and contacting the admixture with a free oxygent-containing gas.

U.S. Pat. No. 3,954,848 to Franz discloses a process for the production of N-phosphonomethylglycine by reacting N-phosphonomethyliminodiacetic acid with an oxidizing agent, such as hydrogen peroxide, in an aqueous acidic medium in the presence of a strong acid at a temperature of from about 70° C. to about 100° C. It is disclosed that one should employ at least 2 moles of the hydrogen peroxide for each mole of the N-phosphonomethyliminodiacetic acid, and preferably more.

Hungarian Patent Application No. 187,347 discloses a process for the preparation of N-phosphonomethylglycine by the oxidation of N-phosphonomethyliminodiacetic acid with peroxides using a catalytic amount of a metal compound selected from compounds of silver, iron, tin, lead, manganese or molybdenum. Molybdates are preferred. At temperatures lower than 80° C., usually a contaminated end product is obtained. Typically, the reaction is carried out at a temperature of above 80° C. and preferably above 100° C. at pressures exceeding atmospheric, wherein the intermediate N-oxide is decomposed as rapidly as it forms. It is further disclosed that at least two mole equivalents of peroxide should be used for each mole equivalent of N-phosphonomethyliminodiacetic acid.

A publication entitled "Peroxygen Compounds in Organic Synthesis" published by *Interox* as a technical bulletin discloses that transition metal compounds, like sodium tungstate or molybdate or the relevant oxides, promote oxidation reactions by a non-radical mechanism. Peroxidic complexes also play a transient role in the metal catalyzed oxidation of olefins and acetylenes by alkyl hydroperoxides.

Although satisfactory results are obtained by the above processes to make N-phosphonomethylglycine, all of them suffer from one or more disadvantages, such as the use of excessive amounts of peroxide, and/or reaction at elevated temperatures and pressures. Now, there is disclosed a process which provides N-phosphonomethylglycine in high yields at modest temperatures and at atmospheric pressure using substantially stoichiometric amounts of peroxide to oxidize the N-phosphonomethyliminodiacetic acid to the desired N-phosphonomethylglycine.

SUMMARY OF THE INVENTION

These and other advantages are achieved in a process for producing N-phosphonomethylglycine by the oxidation of N-phosphonomethyliminodiacetic acid to form an intermediate N-phosphonomethyliminodiacetic acid-N-oxide and converting the intermediate to N-phosphonomethylglycine, the improvement which comprises contacting N-phosphonomethyliminodiacetic acid with a peroxide in the presence of an effective amount of a catalyst selected from the group consisting of water-soluble tungsten compounds and a mixture of a water-soluble tungsten compound and a water-soluble molybdenum compound to form N-phosphonomethyliminodiacetic acid-N-oxide, and thereafter converting the N-phosphonomethyliminodiacetic acid-N-oxide to N-phosphonomethylglycine.

DETAILED DESCRIPTION OF THE INVENTION

The N-phosphonomethyliminodiacetic acid starting material can be prepared by methods known to those skilled in the art. For example, this material can be produced by the reaction of formaldehyde, iminodiacetic acid and orthophosphorous acid in the presence of sulfuric acid. Although the N-phosphonomethyliminodiacetic acid mixture resulting from this reaction can be employed directly in the process of this invention, it is preferred to isolate the N-phosphonomethyliminodiacetic acid and then employ it herein.

Any number of peroxides known to those skilled in the art can be used to prepare the N-phosphonomethyliminodiacetic acid-N-oxide. Suitable peroxides include hydrogen peroxide, performic acid, peracetic acid, perbenzoic acid, peroxytrifluoroacetic acid, benzoyl peroxide, benzenepersulfonic acid, and the like. Hydrogen peroxide is preferred, and it is advantageous to use hydrogen peroxide in the form of a concentrated solution, say between about 30% and 60%.

In the process of the present invention, the N-phosphonomethyliminodiacetic acid-N-oxide is prepared by contacting N-phosphonomethyliminodiacetic acid with a peroxide in the presence of a catalytic amount of a water-soluble tungsten compound or a mixture of a water-soluble tungsten compound and a water-soluble molybdenum compound. Mixtures of a water-soluble tungsten compound and a water-soluble molybdenum compound are preferred.

The temperature of the process to prepare the N-phosphonomethyliminodiacetic acid-N-oxide can vary from as low as about 20° C. to about 70° C. Although temperatures below about 20° C. can be used, such temperatures would require the use of cooling, and no advantages are obtained. At temperatures above about 70° C., degradation of the N-phosphonomethyliminodiacetic acid-N-oxide is observed, which affects the final yield of the desire N-phosphonomethylglycine. Temperatures between about 20° C. and about 65° C. are preferred.

The salts of tungsten useful as catalysts to oxidize the N-phosphonomethyliminodiacetic acid to the N-phosphonomethyliminodiacetic acid-N-oxide are known to those skilled in the art. It is only necessary that the tungsten salts are soluble in the reaction medium. Suitable tungsten compounds include tungstic acid, 1,2-tungstophosphate, and barium tungstate. The alkali metal tungstates, such as sodium tungstate, potassium tungstate, and the like, provide satisfactory results, and the alkali metal tungstates are preferred.

The salts of molybdenum useful in admixture with a water-soluble tungsten compound as catalysts to oxidize the N-phosphonomethyliminodiacetic acid to the N-phosphonomethyliminodiacetic acid-N-oxide are also known to those skilled in the art. It is only necessary that the molybdenum salts are soluble in the reaction medium. Suitable molybdenum compounds include molybdenum halides, such as molybdenyl trichloride and the like, alkali metal molybdates, such as sodium molybdate and the like, or more complex salts, such as the ammonium or alkali metal dimolybdates. Sodium and ammonium molybdates are preferred.

The amount of catalyst to convert the N-phosphonomethyliminodiacetic acid to the intermediate N-phosphonomethyliminodiacetic acid-N-oxide can vary within wide limits. Concentrations between about 0.005 and about 5 wt. % catalyst, based on the weight of the N-phosphonomethyliminodiacetic acid, provide satisfactory results. At concentrations of less than about 0.005 wt. % catalyst, the reaction is slow, and at concentrations greater than about 5 wt. %, no particular advantage is seen, although such higher concentrations are not harmful. It is preferred to use between about 0.01 wt. % and about 1 wt. % based on the weight of the N-phosphonomethyliminodiacetic acid.

When a mixture of a water-soluble tungsten compound and a water-soluble molybdenum compound is used to form the N-phosphonomethyliminodiacetic acid-N-oxide, the ratio of the tungsten compound to the molybdenum compound can vary within wide limits. Satisfactory results have been obtained when the ratio of the tungsten compound to the molybdenum compound varies from about 90:10 to 10:90. However, it is preferred to use a weight ratio of the tungsten compound to the molybdenum compound between about 25:75 and 75:25, and even more preferred to use a weight ratio of tungsten compound to molybdenum compound between about 60:40 and 40:60.

In the process of the present invention, the amount of peroxide should be the stoichiometric amount required to convert the N-phosphonomethyliminodiacetic acid to the intermediate N-phosphonomethyliminodiaceti acid-N-oxide. As will occur to those skilled in the art, when less than the stoichiometric amount of peroxide is used, the yield of the desired N-phosphonomethylglycine is lower. A slight excess of peroxide can be used to insure a quantitative conversion of the N-phosphonomethyliminodiacetic acid to the intermediate, but there is no advantage to using large excesses of peroxide, and excesses of peroxide may be deleterious if water-soluble compounds, such as ferrous sulfate, ferrous halide or an alkali metal metabisulfite compound, is used to convert the intermediate to N-phosphonomethylglycine.

The N-phosphonomethyliminodiacetic acid-N-oxide intermediate is contacted with a catalytic amount of a substance selected from the group consisting of iron metal, the water-soluble salts of a vanadium compound, a ferrous salt, or a mixture of a water-soluble sulfide, sulfite, or bisulfite compound and a water-soluble molybdate compound to convert the intermediate N-phosphonomethyliminodiacetic acid-N-oxide to the desired N-phosphonomethylglycine. Suitable vanadium compounds that are soluble in the reaction mixture include vanadium pentoxide, vanadium sulfate, vanadium chloride and the like. Suitable water-soluble ferrous compounds that can be used in the process of the present invention include ferrous sulfate and ferrous halides, such as ferrous chloride, ferrous bromide and the like. In addition, a sulfide, sulfite or metabisulfite compound, such as sodium sulfide, sodium sulfite, sodium metabisulfite, potassium metabisulfite or ammonium metabisulfite, can be used in a mixture with a water-soluble molybdenum compound, such as molybdenum trichloride, sodium molybdate, ammonium molybdate and the like, to convert the intermediate N-phosphonomethyliminodiacetic acid-N-oxide to the desired N-phosphonomethylglycine.

The amount of catalyst to convert the N-phosphonomethyliminodiacetic acid-N-oxide to N-phosphonomethylglycine depends upon the catalyst used and the amount of peroxide in excess of that required to produce the intermediate from the N-phosphonomethyliminodiacetic acid. When iron metal is used, the rate of reaction to convert the intermediate N-phosphonomethyliminodiacetic acid-N-oxide to N-phosphonomethylglycine depends upon the surface area of the iron metal present, and it is preferred to use from about 1 wt. % to about 10 wt. % of the metal, based on the weight of the N-phosphonomethyliminodiacetic acid-N-oxide present. In addition, it is preferred to use the iron metal in any form that provides a high surface area, for example, a wool, a powder or finely divided granules.

When a water-soluble compound is used as a catalyst to convert the intermediate to N-phosphonomethylglycine, the excess peroxide will react with the water-soluble compound, and in addition to the amount of compound required to react with the excess peroxide, there should also be a sufficient amount of the water-soluble compound to catalyze the reaction of the N-phosphonomethyliminodiacetic acid-N-oxide to N-phosphonomethylglycine. The amount of water-soluble compound remaining after reaction with the peroxide to act as a catalyst should be at least 0.01 wt. %, based on the amount of the N-phosphonomethyliminodiacetic acid-N-oxide. Excess water-soluble compound as high as 10%, even higher, can be used, but there does not seem to be an advantage to using such higher concentrations for the conversion of the intermediate to N-phosphonomethylglycine, although such higher concentrations are not harmful. It is preferred to use between about 0.01 wt. % and about 1 wt. % of the water-soluble compound, based on the weight of the N-phosphonomethyliminodiacetic acid-N-oxide, after reaction with any excess peroxides.

The temperature required to convert the intermediate N-phosphonomethyliminodiacetic acid-N-oxide to the desired N-phosphonomethylglycine can vary within wide limits. It is preferred to add the catalyst at or near room temperature (about 20° C.) because vigorous gas evolution frequently occurs, and the conversion of N-phosphonomethyliminodiacetic acid-N-oxide to N-phosphonomethylglycine is exothermic. It is preferred to keep the reaction temperature below about 80° C. by cooling the reaction vessel or using a low catalyst charge. Temperatures above about 80° C. will provide N-phosphonomethylglycine, but some yield loss may occur.

The concentration of the N-phosphonomethyliminodiacetic acid as the starting material can vary within wide limits in the process of the present invention. For example, an aqueous suspension containing up to 50 wt. % N-phosphonomethyliminodiacetic acid can be used. Higher concentrations of the N-phosphonomethyliminodiacetic acid can be used, but it can present processing difficulties because of the thickness of the slurry. On the other hand, an aqueous solution of the N-phosphonomethyliminodiacetic acid containing about 5 wt. % of the N-phosphonomethyliminodiacetic acid can also be used. Lower concentrations can also be used, but it requires processing large volumes of liquid in the process of the present invention. It is preferred to use an aqueous slurry containing from about 20 wt. % to about 40 wt. % of the N-phosphonomethyliminodiacetic acid.

This invention is further illustrated by, but not limited to, the following examples. Conversion is calculated by dividing the moles of other compounds produced by the moles of starting N-phosphonomethyliminodiacetic acid and multiplying by 100. Selectivity is calculated by dividing the moles of N-phosphonomethylglycine produced by the moles of N-phosphonomethyliminodiacetic acid converted and multiplying by 100.

EXAMPLE 1

This Example illustrates the process of the present invention using a water-soluble tungsten salt to convert N-phosphonomethyliminodiacetic acid to the intermediate N-phosphonomethyliminodiacetic acid-N-oxide, and the subsequent formation of N-phosphonomethylglycine.

(A) To a 100 ml round bottomed flask was added water (25 ml), N-phosphonomethyliminodiacetic acid (20 g), 47% hydrogen peroxide (7.1 g) and sodium tungstate (0.05 g). The mixture was heated to 65° C. and maintained at this temperature until a solution was obtained (about 58 minutes), indicating the N-oxide was formed. The solution was then allowed to cool to about 55° C. and stirred for an additional 30 minutes.

(B) After cooling to room temperature, vanadyl sulfate (0.05 g, 29% $H_2O$) was added to the solution. After stirring for about 5 minutes, the color of the solution changed from blue to light green. Gas evolution began with a slow exotherm. When the temperature reached about 40° C., the exotherm greatly accelerated to 65° C. and cooling water was applied to maintain the solution at this temperature. The reaction mixture was allowed to cool to room temperature, the solids were filtered, and the filtrate and solids were analyzed by HPLC. The conversion of N-phosphonomethyliminodiacetic acid was 96.7%, and the selectivity to N-phosphonomethylglycine was 91.4%.

EXAMPLE 2

This Example illustrates the process of the present invention using a mixture of a water-soluble tungsten salt and a water-soluble molybdenum salt to convert N-phosphonomethyliminodiacetic acid to the intermediate N-phosphonomethyliminodiacetic acid-N-oxide, and the subsequent formation of N-phosphonomethylglycine.

(A) To a 100 ml round bottomed flask was added water (25 ml), N-phosphonomethyliminodiacetic acid (20 g), 47% hydrogen peroxide (7.1 g), sodium tungstate (0.05 g) and sodium molybdate (0.05 g). The mixture was heated to 65° C. and maintained at this temperature until a solution was obtained (about 52 minutes), indicating that the N-oxide was formed. The solution was then allowed to cool to about 55° C. and stirred for an additional 1 hour and 45 minutes.

(B) After cooling to room temperature, sodium metabisulfite (0.45 g) was added to the solution. After stirring for about 5 minutes, gas evolution was observed with a slow exotherm. When the temperature reached about 40° C., the exotherm greatly accelerated to 65° C. and cooling water was applied to maintain the solution at this temperature. The reaction mixture was allowed to cool to room temperature, the solids were filtered, and the filtrates and the solids were analyzed by HPLC. The conversion of N-phosphonomethyliminodiacetic acid was 91.8%, and the selectivity to N-phosphonomethylglycine was 96.3%.

Although the invention has been described in terms of specified embodiments which are set forth in considerable detail, it should be understood that this is by way of illustration only, and that alternative embodiments and operating techniques will become apparent to those skilled in the art in view of the disclosure. Accordingly, modifications can be made without departing from the spirit of the described invention.

What is claimed is:

1. In a process for producing N-phosphonomethylglycine by the oxidation of N-phosphonomethyliminodiacetic acid to form an intermediate N-phosphonomethyliminodiacetic acid-N-oxide and converting the intermediate to N-phosphonomethylglycine, the improvement which comprises contacting N-phosphonomethyliminodiacetic acid with a peroxide in the presence of an effective amount of a catalyst selected from the group consisting of a water-soluble tungsten compound, and a mixture of a water-soluble tungsten compound and a water-soluble molybdenum compound, to form N-phosphonomethyliminodiacetic acid-N-oxide, and thereafter converting the N-phosphonomethyliminodiacetic acid-N-oxide to N-phosphonomethylglycine.

2. In the process of claim 1 wherein the amount of catalyst is between about 0.005 wt. % and about 5 wt. %, based on the weight of the N-phosphonomethyliminodiacetic acid.

3. In the process of claim 2 wherein the amount of catalyst is between about 0.01 wt. % and about 1 wt. %.

4. In the process of claim 2 wherein the catalyst is a mixture of a water-soluble tungsten compound and a water-soluble molybdenum compound.

5. In the process of claim 4 wherein the weight ratio of tungsten compound to molybdenum compound is from about 10:90 to about 90:10.

6. In the process of claim 5 wherein the weight ratio of tungsten compound to molybdenum compound is from about 25:75 to 75:25.

7. In the process of claim 6 wherein the weight ratio of tungsten compound to molybdenum compound is from about 40:60 to about 60:40.

8. In the process of claim 1 wherein the catalyst is a tungsten compound.

9. In the process of claim 8 wherein the tungsten compound is selected from the group consisting of the alkali metal tungstates.

10. In the process of claim 9 wherein the tungsten compound is sodium tungstate.

11. In the process of claim 1 wherein the peroxide is hydrogen peroxide.

12. In the process of claim 5 wherein the tungsten compound is an alkali metal tungstate and the molybdenum compound is an alkali metal molybdate or ammonium molybdate.

13. In the process of claim 1 wherein the temperature to form the N-phosphonomethyliminodiacetic acid-N-oxide is between about 20° C. and about 70° C.

* * * * *